(12) United States Patent
McNeel et al.

(10) Patent No.: US 9,347,928 B2
(45) Date of Patent: May 24, 2016

(54) TAGGED POLYMERS, WATER TREATMENT COMPOSITIONS, AND METHODS OF THEIR USE IN AQUEOUS SYSTEMS

(75) Inventors: Thomas E. McNeel, Memphis, TN (US); Marilyn S. Whittemore, Memphis, TN (US); Richard A. Clark, Memphis, TN (US); Jadwiga J. Grabowicz, Memphis, TN (US)

(73) Assignee: Buckman Laboratories International, Inc., Memphis, TN (US)

( * ) Notice: Subject to any disclaimer, the term of this patent is extended or adjusted under 35 U.S.C. 154(b) by 860 days.

(21) Appl. No.: 13/561,455

(22) Filed: Jul. 30, 2012

(65) Prior Publication Data

US 2013/0043194 A1 Feb. 21, 2013

Related U.S. Application Data

(60) Provisional application No. 61/524,594, filed on Aug. 17, 2011.

(51) Int. Cl.
| | |
|---|---|
| *C02F 1/52* | (2006.01) |
| *G01N 33/18* | (2006.01) |
| *C09K 11/06* | (2006.01) |
| *C02F 1/00* | (2006.01) |

(52) U.S. Cl.
CPC ............ *G01N 33/1826* (2013.01); *G01N 33/18* (2013.01); *C02F 1/008* (2013.01); *C02F 1/5209* (2013.01); *C02F 2209/06* (2013.01); *C02F 2303/20* (2013.01); *C09K 11/06* (2013.01); *Y10S 210/917* (2013.01); *Y10T 436/13* (2015.01)

(58) Field of Classification Search
CPC ....... C02F 1/5209; C02F 1/441; G01N 33/00; G01N 33/18; Y10T 436/13; Y10S 210/917; C09K 11/06

USPC .................... 436/56; 210/745, 605, 611, 620; 526/259
See application file for complete search history.

(56) References Cited

U.S. PATENT DOCUMENTS

| 4,783,314 A | 11/1988 | Hoots et al. |
| 4,992,380 A | 2/1991 | Moriarty et al. |

(Continued)

OTHER PUBLICATIONS

Fluorescence Experiments with Quinine, p. 610-612. O' Reilly 1975.*

(Continued)

*Primary Examiner* — Krishnan S Menon
*Assistant Examiner* — Waqaas Ali
(74) *Attorney, Agent, or Firm* — Kilyk & Bowersox, P.L.L.C.

(57) ABSTRACT

A method and composition is described for controlling the growth of fouling materials, such as scale, in aqueous systems using a tagged (fluorescent) polymer. The tagged polymer can be a fluorescent polymer which has at least one fluorescent monomeric unit derived from a fluorophore which has at least one terminal end comprising an olefinic group. The method of controlling the growth of at least one fouling material in an aqueous system can include the steps of adding the tagged polymer to the aqueous system to be treated, fluorometrically monitoring the concentration of the tagged polymer, and adjusting, as needed, the concentration of the tagged polymer and proportionally used water treatment compound or compounds effective to control the growth of at least one fouling material. The adjustment of pH before determination of the fluorescence signal can be employed to increase sensitivity of the fluorophore and minimize background interference.

16 Claims, 4 Drawing Sheets

Quinine

Quinidine

(56) References Cited

U.S. PATENT DOCUMENTS

| | | | | |
|---|---|---|---|---|
| 5,128,419 | A * | 7/1992 | Fong | C08F 8/34 525/329.4 |
| 5,171,450 | A | 12/1992 | Hoots | |
| 5,278,074 | A * | 1/1994 | Rao | G01N 21/64 436/163 |
| 5,691,428 | A * | 11/1997 | Shimizu | B01J 19/002 526/344.2 |
| 5,704,656 | A * | 1/1998 | Rowe | 285/93 |
| 5,971,444 | A * | 10/1999 | Hawkins | 285/206 |
| 5,986,030 | A | 11/1999 | Murray et al. | |
| 6,288,177 | B1 * | 9/2001 | Ooura | C08F 2/004 526/344.2 |
| 6,310,156 | B1 | 10/2001 | Maeda et al. | |
| 6,312,644 | B1 | 11/2001 | Moriarty et al. | |
| 6,790,664 | B2 * | 9/2004 | Bailey | G01N 21/643 436/172 |
| 7,179,384 | B2 | 2/2007 | Moriarty et al. | |
| 7,301,158 | B1 | 11/2007 | Hoang | |
| 7,413,651 | B2 * | 8/2008 | Hodak | 210/167.19 |
| 7,875,720 | B2 | 1/2011 | Morris et al. | |
| 8,152,538 | B1 * | 4/2012 | Papageorge | 439/100 |
| 2005/0242042 | A1 * | 11/2005 | Moriarty et al. | 210/696 |
| 2006/0278289 | A1 * | 12/2006 | Robinson | 138/40 |
| 2015/0148266 | A1 * | 5/2015 | Webber | C09K 8/52 507/90 |
| 2015/0184069 | A1 * | 7/2015 | Nuutinen | C09K 11/06 210/700 |

OTHER PUBLICATIONS

Characterization of Quinine and Its Determination, Sawyer, 2010.*
Written Opinion of the International Preliminary Examining Authority issued in corresponding International Patent Application No. PCT/US2012/048803 dated Sep. 4, 2013 (7 pages).
International Search Report issued in corresponding International Patent Application No. PCT/US2012/048803 dated Nov. 9, 2012 (8 pages).
Hu, et al., "Synthesis and Chiral Micellization Behavior of Optically Active Amphiphilic Diblock Copolymer Bearing Quinine Pendants," Journal of Polymer Science Part A: Polymer Chemistry, vol. 47, No. 14, pp. 3640-3650, Jul. 15, 2009.
Borchan, et al., "Copolymerization of N-vinylpyrrolidone with Quinine," Polymer Science U.S.S.R., Pergamon, vol. 29, No. 1, pp. 43-49, Jan. 1, 1987.
International Search Report and Written Opinion issued in corresponding International Patent Application No. PCT/US2012/048803 dated Jan. 18, 2013 (15 pages).

* cited by examiner

Quinine

Quinidine

FIG. 4

Table 1

| Tagged Polymer (ppm) Run | 0.05 H₂SO₄ (pH 1.86) | | | Cooling Tower (pH 1.86) | | | 150 ppm Cl⁻ | | | 500 ppm Cl⁻ | | |
|---|---|---|---|---|---|---|---|---|---|---|---|---|
| | Day 1 | Day 2 | Day 5 | Day 1 | Day 2 | Day 5 | Day 1 | Day 2 | Day 5 | Day 1 | Day 2 | Day 5 |
| Run 1 | | | | | | | | | | | | |
| 1 ppm | 16.5 | 11.2 | 11.1 | 19.3 | 13.4 | 12.9 | 10.3 | 10.7 | 11.1 | 7.9 | 7.8 | 8.2 |
| 5 ppm | 68.6 | 48.3 | 46.2 | 69.7 | 48.6 | 55 | 34.3 | 35.1 | 50.1 | 20.4 | 19.7 | 21.2 |
| 10 ppm | 132 | 92.1 | 90.2 | 128.2 | 89.3 | 90.1 | 63.2 | 63.8 | 63.5 | 35.4 | 34.7 | 35.7 |
| 20 ppm | off scale | off scale | off scale | off scale | off scale | off scale | 114.8 | 116.3 | 114 | 63.7 | 62.7 | 57.5 |
| Run 2 | | | | | | | | | | | | |
| 1 ppm | 11.2 | 11.8 | 11.5 | 16.6 | 15.7 | 16.7 | 13.5 | 13.7 | 13.2 | 9.1 | 9.1 | 9.5 |
| 5 ppm | 50.5 | 50.1 | 49.5 | 51.6 | 51.6 | 52.5 | 39.0 | 39.6 | 34.9 | 24.3 | 24.0 | 24.6 |
| 10 ppm | 95.3 | 94.1 | 94.7 | 92.0 | 90.8 | 92.8 | 67.1 | 67.5 | 71.5 | 42.7 | 41.8 | 43.4 |
| 20 ppm | off scale | off scale | off scale | off scale | off scale | off scale | 124.6 | - | - | 76.7 | 76.2 | 78.3 |
| Run 3 | | | | | | | | | | | | |
| 1 ppm | 12.2 | 11.4 | 11.5 | 16.1 | 18.5 | 16.5 | 12.3 | 13.5 | - | 9.5 | 9.1 | 9.6 |
| 5 ppm | 50.9 | 51.2 | 50.3 | 52.7 | 53.9 | 53.2 | 37.8 | 38.9 | - | 23.6 | 23.5 | 24.8 |
| 10 ppm | 96.4 | 95.2 | 95.6 | 91.0 | 90.9 | 91.6 | 66.8 | 70.8 | - | 40.9 | 40.4 | 46.0 |
| 20 ppm | off scale | off scale | off scale | off scale | off scale | off scale | 123.8 | 124.8 | - | 73.8 | 72.9 | 82.6 |
| Run 4 | | | | | | | | | | | | |
| 1 ppm | 13.8 | 13.4 | 13.4 | 18.0 | 19.0 | 18.9 | 14.3 | 16.4 | - | 9.5 | 10.1 | 9.6 |
| 5 ppm | 55.0 | 54.5 | 54.4 | 58.1 | 56.1 | 57.3 | 42.4 | 42.1 | - | 24.4 | 24.9 | 24.8 |
| 10 ppm | 106.3 | 106.3 | 101.4 | 104.3 | 103.9 | 105.1 | 77.6 | 78.4 | 78.3 | 45.4 | 44.4 | 46.0 |
| 20 ppm | off scale | off scale | off scale | off scale | off scale | off scale | off scale | off scale | off scale | 82.5 | 81.2 | 82.6 |

TAGGED POLYMERS, WATER TREATMENT COMPOSITIONS, AND METHODS OF THEIR USE IN AQUEOUS SYSTEMS

This application claims the benefit under 35 U.S.C. §119 (e) of prior U.S. Provisional Patent Application No. 61/524,594, filed Aug. 17, 2011, which is incorporated in its entirety by reference herein.

FIELD OF THE INVENTION

The present invention relates to tagged polymers and compositions including them, which can be used in controlling fouling materials in aqueous systems or other uses. The present invention also relates to methods for controlling fouling in industrial water systems or other aqueous systems using the tagged polymers, and to methods to monitor concentrations of polymers in systems.

BACKGROUND OF THE INVENTION

Many conventional aqueous systems, such as industrial cooling water systems and others, have used treatment products to control undesirable fouling, such as scaling, corrosion, and microbiological growth. The fouling control materials have been used, for example, to control formation of scale or other fouling materials on substrate surfaces in contact with the water in the system. The fouling control materials also have been used, for example, to control the presence of the fouling material suspended in the water. Fouling control materials have included inorganic and organic materials. Polymers, for example, have been used to control scale and other fouling materials in aqueous systems. A treatment polymer added to water of an aqueous system can be consumed for one or more various reasons, for example, it may be consumed as it performs a desired function to control a fouling material, or be lost in blowdown of a cooling system, or for other reasons. Monitoring of the concentration of a treatment polymer in the water of the water system and replacement of lost amounts of treatment polymer has been done to maintain fouling control.

Various analytical methods have been used to measure the amount of the treatment polymer added to the water in industrial water systems. Inert (i.e., non-treating) fluorescent tracer compounds and methods of using them have been shown, for example, in U.S. Pat. Nos. 4,783,314; 4,992,380; and 5,171,450. Other fouling control agents that have been used in industrial water systems are polymers tagged with a fluorescent repeating unit or monomer. As shown, for example, in U.S. Pat. No. 5,986,030, a concentration of a treatment polymer has been determined using a fluorometer to measure the fluorescent signal of a fluorescent repeating unit or monomer thereof. Tagged polymers which incorporate chemically-synthesized quaternary salt fluorescent monomers are shown, for example, in U.S. Pat. Nos. 7,179,384 B2 and 7,875,720 B2. Some prior tagged polymers have required chemical synthesis of both the fluorescent monomers and the polymers incorporating these constituents. Additional cost and production complexity can occur if synthetic monomers must be manufactured before they can be incorporated into tagged polymers.

The present investigators have recognized that it is desirable to have a method of controlling the growth of scale or other fouling materials in aqueous systems which can use tagged polymers, which can be more easily obtained without need of extensive chemical syntheses, and/or which tagged polymers can be accurately detected and monitored in an aqueous system at relatively low concentrations, which are compatible with other water treating agents, and which are environmentally-friendly. The present investigators also have recognized a need to address background noise and interference which can affect the accuracy and consistency of spectrophotometric or spectrofluorometric monitoring and dosing of water treatment materials into the aqueous system under treatment.

SUMMARY OF THE INVENTION

A feature of this invention is to provide a method of controlling the concentration of a water treatment polymer in an aqueous system using an improved tagged polymer.

An additional feature of this invention is to provide a method of controlling the growth of scale or other fouling materials in an aqueous system which can use improved tagged polymers and indicator constituents thereof, which can be more readily obtained without requiring extensive or complicated chemical syntheses.

A further feature of this invention is to provide new fluorescent polymers useful for water treatment methods and systems, which can be accurately monitored at relatively low concentrations in the systems, which can be compatible with other water treating agents used in the same system, and/or which can be more environmentally-friendly ("green").

Another feature of this invention is to provide water treatment compositions including improved tagged polymers and, optionally, with one or more other water treatment chemicals or additives.

Additional features and advantages of the present invention will be set forth in part in the description which follows, and in part will be apparent from the description, or may be learned by practice of the present invention. The objectives and other advantages of the present invention will be realized and obtained by means of the elements and combinations particularly pointed out in the written description and appended claims.

To achieve these and other advantages and in accordance with the purposes of the present invention, as embodied and broadly described herein, the present invention, in part, relates to a method for controlling concentration of a water treatment polymer in an aqueous system, which comprises introducing, into the aqueous system, a water treatment composition comprising a tagged polymer and, optionally, at least one different water treatment chemical, to provide treated water. The tagged polymer comprises at least one fluorescent monomeric unit derived from a fluorophore having at least one terminal end comprising an olefinic group. The tagged polymer is pH sensitive. A sample of the treated water can be extracted, and the pH of the extracted sample can be adjusted to provide an enhanced fluorescence signal. The enhanced fluorescence signal is measured and the concentration of the tagged polymer in the sample can be determined using the measured enhanced fluorescence signal. If at least one different water treatment chemical or additive is used, then knowing the proportion of the introduced tagged polymer and at least one different water treatment chemical, a concentration of the different water treatment chemical can be determined, for example, from the determined concentration of the tagged polymer. The determined concentration of the tagged polymer can be compared to a selected low limit set point, and if the determined concentration is less than the selected low limit set point, the concentration of the tagged polymer and optionally the concentration of at least one different water treatment chemical can be adjusted in the aqueous system by adding a fresh amount of the water treatment composition into the aqueous system. The added fresh amount of the water treatment composition can be an amount that at least partly makes-up for the detected deficiency of the concentration of the treatment composition in the treated system. This succession of steps can be repeated any number of times over a monitoring period. The different water treatment chemical(s) can be polymeric, nonpolymeric, or comprise combinations or mixtures of both types of treatment chemicals. The method can maintain amounts of the water treatment composition in the aqueous system in amounts wherein it can interact with the aqueous system sufficiently to control the accumulation of at least one fouling material in the aqueous system.

The present invention further relates to one or more tagged polymers, which can be used in the indicated water treatment method or other methods, which comprise at least one fluorescent monomeric unit derived from a fluorophore having at least one terminal end comprising an olefinic group and at least one different monomeric unit. The tagged polymer is pH sensitive, such that in adjusting the pH, the fluorescence of the tagged polymer can be enhanced (e.g., increased). The fluorophore can comprise, for example, quinine or an isomer thereof, such as quinidine. The tagged polymer can be, for example, a terpolymer or copolymer of quinine or an isomer thereof, with at least one different monomer. The different monomer can be, for example, acrylamide, acrylic acid or salts thereof, methacrylic acid or salts thereof, maleic acid or salts thereof, maleic anhydride, crotonic acid or salts thereof, itaconic acid or salts thereof, methacrylamide, 2-acrylamido-2-methylpropane sulfonic acid (AMPS) or salts thereof, polyethylene glycol monomethacrylate, vinyl phosphonic acid or salts thereof, styrene sulfonic acids or salts thereof, vinyl sulfonic acid or salts thereof, 3-allyloxy-2-hydroxypropane sulfonic acid or salts thereof, N-alkyl-(meth)acrylamide, t-butyl(meth)acrylate, N-alkyl(meth)acrylate, N-alkanol-N-alkyl(meth)acrylate, dimethyldiallyl ammonium chloride (DMDAAC, or DADMAC), vinyl acetate, 2-hydroxy N-alkyl (meth)acrylate, alkyl vinyl ether, alkoxyethyl acrylate, N-alkanol (methyacrylamide, N,N-dialkyl(meth)acrylamide, vinyl-2-pyrrolidinone, or any monomer(s) with double bond functionality, or any combinations thereof.

The present invention further relates to tagged polymers, which can be used in the indicated water treatment method or other methods. In these polymers, a hydroxyl functionality is maintained, thus allowing the pH sensitivity to remain, and thus the tagged polymers are considered pH sensitive. This feature differs from previous materials employed in the industry. Adjusting the pH allows reduction or elimination of background interference, thus improving the accuracy and precision with which the polymer dosing is monitored. Fluorophores which can be used in this regard include, for example, quinine and quinidine. Quinine and quinidine are natural products, "green" chemistry, which have some accepted dietary and pharmacological uses. Quinine, for example, has been used medicinally as an antimalarial and also in the food/beverage industry while quinidine, for example, has been used as an antipyretic and depressant of cardiac fibrillation, and their different pharmacological actions are the result of their different geometries.

The polymer may have one, two, or three monomers in addition to the fluorescent monomer. Free radical or redox initiation of the polymerization process would incorporate the quinine (quinidine) into the polymer backbone.

The quinine or isomer thereof can be used, for example, as a minor component of the polymer and provide fluorescence performance suitable for water treatment polymer monitoring and control of fouling material in aqueous systems. The other monomeric unit(s) in the tagged polymer, in one option, can have a fouling control property or effect, in a treated aqueous system. The tagged polymer can be, for example, a monitoring polymer, a water-treating polymer, or both.

The present invention further relates to water treatment compositions including the indicated tagged polymer and optionally at least one different water treatment chemical.

The present invention can be applied in a variety of aqueous systems and processes, including but not limited to, cooling water systems (e.g., cooling tower systems), both open and closed recirculating water systems, fire water systems, decorative fountains, air washers, sterilizers, retort system, heat exchangers, boilers, water heaters, swimming pools, drinking water systems, hot tubs, influent water systems, effluent water system, and other industrial, recreational, or residential water systems.

For purposes herein, "fouling" can be or include the accumulation of unwanted material on solid surfaces contacted by water of an aqueous system, or material suspended in water of an aqueous system, or both. A "fouling material" can be, for example, a nonliving substance (inorganic or organic), or a living organism, or both. The fouling material can be, for example, scale, corrosion, oils, greases and/or organic contaminants from process leaks, microbial organisms, algae, suspended solids, or any combinations thereof. The fouling material to be controlled can be scale alone. Control of fouling can be used to prevent or reduce the amount or concentration of at least one fouling material, such as scale, in the aqueous system.

The term "control," in reference to the growth of at least one fouling material, can be, for example, the reduction or prevention of new growth, or the reduction or complete elimination of existing growth, in the aqueous system under treatment.

The term "tagged polymer" can refer to a fluorescent polymer which can be detected with fluorometry and quantitated in samples extracted from a composition or system containing them.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

It is to be understood that both the foregoing general description and the following detailed description are exemplary only and are not restrictive of the present invention, as claimed. All patents, patent applications, and publications mentioned above and throughout the present application are incorporated in their entirety by reference herein.

The accompanying drawings, which are incorporated in and constitute a part of this application, illustrate some of the features of the present invention and together with the description, serve to explain the principles of the present invention.

BRIEF DESCRIPTION OF THE DRAWINGS

FIG. 4 shows Table 1, which includes results of experiments described in the Examples herein, wherein the emission intensities of samples treated with fluorescent (tagged) polymers, which were used in different (ppm) concentrations in different aqueous systems, were measured with fluorometry (fluorescence spectrometry) at several different times.

DETAILED DESCRIPTION

Figure 1:
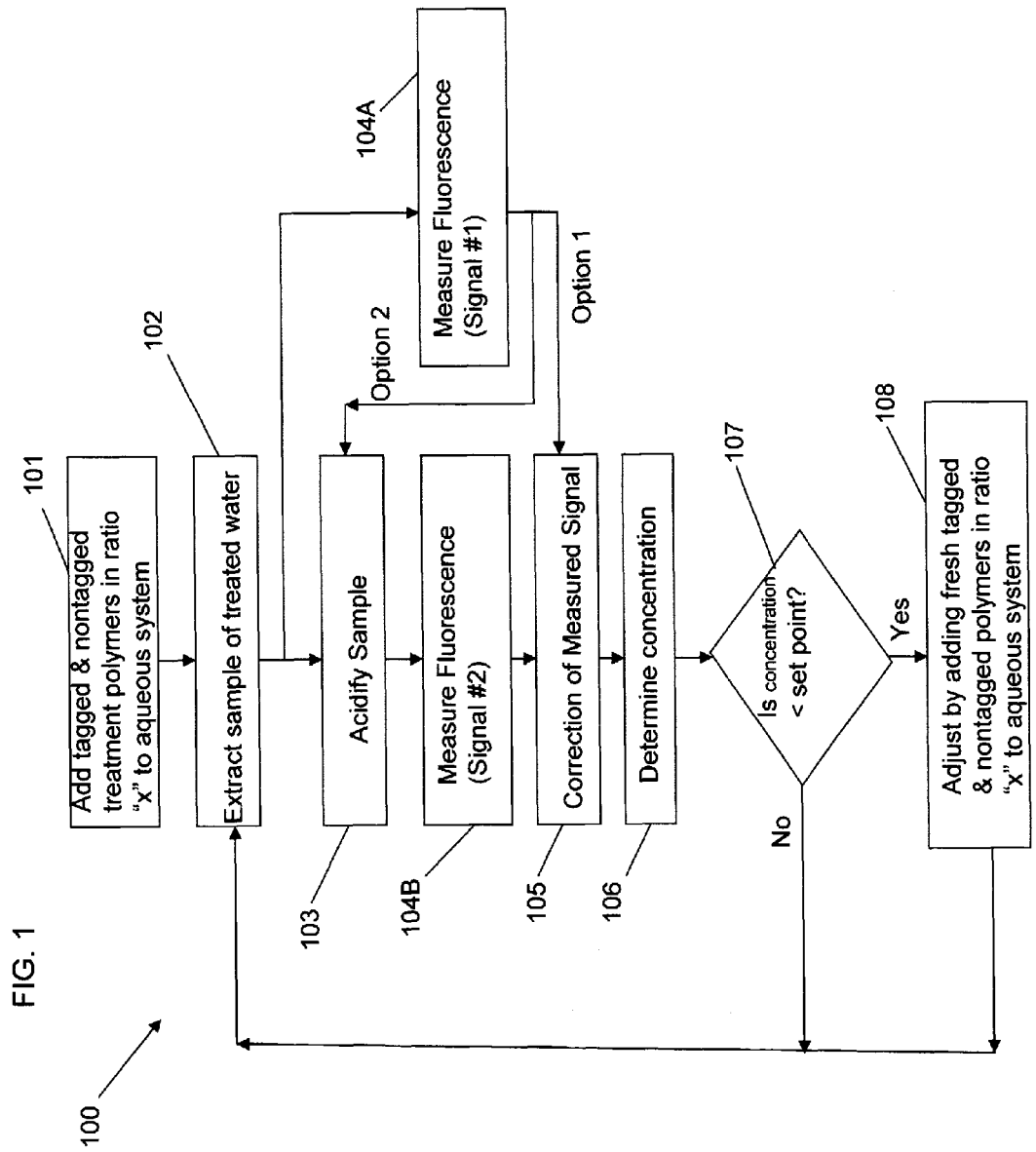
FIG. 1 is a process flow chart of a method for controlling the concentration of a water treatment composition containing a tagged polymer and optionally at least one different water treatment chemical in an aqueous system according to an example of the present invention.

The present invention provides methods and compositions for controlling the growth of fouling material in aqueous systems, or other uses, with use of an improved tagged polymer. In more detail, the tagged polymer can be or include a fluorescent polymer which has at least one fluorescent monomeric unit derived from a fluorophore which has at least one terminal end comprising an olefinic group. The tagged polymer can have and maintain at least one hydroxyl functionality on the fluorophore to retain the pH sensitivity. Thus, the tagged polymer of the present invention can be considered pH sensitive. The tagged polymer that is pH sensitive and that includes a fluorescent component can have the fluorescent signal or fluorescence enhanced by adjusting the pH of the tagged polymer or the solution or system that contains the tagged polymer. The tagged polymer can be used, for example, in water treatment compositions. The tagged polymer or at least one different monomeric unit of the tagged polymer, in one option, can have a fouling control property or effect, such as scale control, in an aqueous system being treated. Changing the pH of a solution containing the tagged polymer or composition containing same before or after at least one fluorometric measurement can mask out background noise or interference or otherwise provide a more accurate and precise signal correlated to the quantity of tagged polymer in the sample. In this way, a more consistent and accurate method and system for monitoring treatment compound levels in an aqueous system, such as an industrial water system, can be provided. With regard to changing the pH, as indicated, the tagged polymers of the present invention are pH sensitive. Depending on the chemistry of the fluorophore functionality (or fluorescent component) that is present in the tagged polymer, the fluorescence or fluorescent signal can be enhanced (e.g., increased) by adjusting the pH of the fluorophore functionality (or fluorescent component) that is present in the tagged polymer. Typically, adjusting the pH can occur by adjusting the overall pH of the aqueous solution containing the tagged polymer. Depending on the fluorophore functionality (or fluorescent component) that is present in the tagged polymer, enchancing the fluorescence or fluorescent signal can be accomplished either by raising the pH or lowering the pH. For instance, when the fluorophore is derived from a quinine or an isomer thereof, the enchancing of the fluorescent signal is accomplished by lowering the pH with, for instance, an acid. Those skilled in the art know whether the fluorescent signal can be enhanced by raising the pH or lowering the pH based on the particular fluorophore chemistry present in the tagged polymer as long as the fluorophore is pH sensitive. For purposes of the present invention, the water treatment composition of the present invention can be considered pH sensitive, and/or the tagged polymer can be considered pH sensitive, and/or the fluorophore component that is present as part of the tagged polymer can be considered pH sensitive, and/or the sample or solution containing the tagged polymer can be considered pH sensitive. In each of these cases, the pH sensitivity is at least provided in part, if not entirely, by the fluorophore component present in the tagged polymer, which is pH sensitive. The adjustment of the pH can be by any amount. For instance, the adjustment of the pH can be a change of pH (based upon the non-adjusted pH value of the solution containing the tagged polymer) of 0.1 or greater, such as 0.2, 0.5, 0.7, 1, 1.2, 1.5, 1.7, 2, 2.2, 2.5, 2.7, or 3 or more with regard to a pH change. As a further example, the tagged polymer of the present invention can comprise at least one fluorophore (or fluorophore component or functionality) that is pH sensitive and at least monomeric unit (different from the fluorophore) that has at least one water treatment property, such as the ability to provide scale control and/or anti-fouling properties.

The tagged polymers can be used as scale or other fouling material inhibitors in industrial water systems or other aqueous systems. The tagged polymer(s) used can be considered active ingredients as water treatment chemicals and have the ability themselves to control fouling, such as scaling. As these tagged polymers can be consumed performing that fouling control function, or for other reasons, the fluorescence signal of a tagged polymer in an aqueous system can decrease over time of use and such a detected decrease in the fluorescence signal can be used to indicate that undesired scaling or other fouling may be taking place in the system and/or that the concentration of the tagged polymers otherwise has been reduced within the system. A method of controlling the growth of at least one fouling material in an aqueous system can include the steps of adding the tagged polymer to the aqueous system to be treated, fluorometrically monitoring the concentration of the tagged polymer, and adjusting, as needed, the concentration of the tagged polymer and, optionally, any other water treatment chemical(s) (that may be present) effective to control the growth of at least one fouling material in the aqueous system. These adjustments can be made to the treatment of the aqueous systems in real time or substantially real time. The effective concentration or concentration range of the water treatment composition(s) can vary in accordance with the particular treatment material(s) and particularities of the aqueous system to be treated and can be determined by one skilled in the art in view of the disclosure provided herein.

The methods of the present invention are useful in preserving or controlling the growth of fouling material in various types of aqueous systems susceptible to attack by them. The aqueous systems which can be treated with the present water treatment compositions can be, for example, cooling water systems, heat exchangers, boilers, water heaters, recirculating water systems, drinking water systems, recreational water, influent plant water, effluent water, and other aqueous systems. A cooling water system can comprise, for example, a cooling tower, heat exchangers, pumps and piping necessary to convey water throughout the system. One or more of these locations may be susceptible to scale or other fouling material formation or other problems without appropriate treatment with active water treatment agents dispersed in the water of the system at suitable, but preferably not excessive (and more costly), levels in a sustained manner.

The fluorescent monomer need not require intensive chemical synthesis, and polymers made with this fluorescent monomer can be effectively monitored at relatively low concentrations (e.g., at less than about 20 ppm tagged polymer, or other values such as described herein). Another advantage of tagged polymers of this invention is that the fluorescent monomer constituent thereof can be relatively stable, wherein it is not significantly affected by other structures in the polymer or by other ingredients in the system. The tagged polymer can be capable of functioning as anti-fouling material in its own right in the aqueous system. As an option, the tagged polymer can be used as a minor component (for instance, as a tracer) in combination with other water treating agents, chemicals, or materials introduced into the aqueous system to be treated, with the amount of tagged polymer maintained sufficient at least for monitoring purposes, such as described herein. As an option, the treatment composition can include at least one water treatment chemical or additive which can be essentially the same as the tagged polymer, but without the fluorescent monomer, or can be otherwise different from the tagged polymer. If at least water treatment chemical or additive is present along with the tagged polymer(s), it is advantageous that the water treatment chemical or additive that is not the tagged polymer have similar chemistry to the tagged polymer since the water treatment chemical or additive having similar chemistry will or should react and/or otherwise affect the system being treated, such that the reduction in concentration of the similar water treatment chemical or additive will be the same, or very similar to, the tagged polymer since the tagged polymer will have the same active components as part of the tagged polymer, but also the fluorescent monomer. For purposes of the present invention, however, if one or more water treatment chemicals or additives or present, the chemistry of the water treatment chemical or additive (e.g., non-tagged polymer) can be the same or different from the tagged polymer with respect to the active chemistry or active polymeric units present that is capable of controlling fouling in a system.

The present methods can control the formation of organic and/or inorganic scale deposits, and/or inhibit corrosion by limiting differential oxidation conditions associated with foulants, and/or reduce microbiological proliferation and/or its consequences (biofouling and microbiologically-induced corrosion (MIC), or any combinations of these). As indicated, in the methods of the present invention, the present compounds and compositions can be used to control of the growth of at least one fouling material in the aqueous system. For example, the "control" of the growth of at least one fouling material can mean the growth of the fouling material is prevented, wherein there is no growth or essentially no growth of the fouling material. The "control" of the growth of at least one fouling material alternatively can mean the action of the water treatment agent to reduce scale-build-up completely (even to undetectable limits, e.g., zero build-up) or at least to a smaller level than would occur in the system without treatment. Treatment of aqueous systems susceptible to fouling material formation with the present compounds and compositions can, for example, avoid or at least reduce the rate of this build-up and the resulting detrimental effects caused by the fouling material.

Referring to FIG. 1, a method 100 of controlling the concentration of a water treatment composition in an aqueous system is shown including steps 101, 102, 103, 104A-B, 105, 106, 107, and 108. In step 101, a water treatment composition comprising a tagged polymer (e.g., a fluorescent polymer) can be introduced in a selected or known ratio "x" or proportion to at least one different water treatment chemical to an aqueous system to provide treated water. The tagged polymer comprises at least one fluorescent monomeric unit derived from a fluorophore having at least one terminal end comprising an olefinic group. The tagged polymer is described in further detail in other sections herein. In step 102, a sample of the treated water is extracted. An aliquot of the extracted sample is adjusted with respect to pH (e.g., acidified) in step 103 prior to fluorometry analysis in step 104B, and another aliquot is directly subjected to fluorometry analysis in step 104A without adjustment of pH. In step 104A, a fluorescence signal (e.g., the relative emission intensity) of the extracted sample can be measured ("Signal #1") using a predetermined appropriate excitation wavelength (e.g., the peak or maximum absorption wavelength) and with relative emission intensity measured at a predetermined appropriate emission wavelength (e.g., the peak or maximum emission wavelength) for the tagged polymer being used. In step 104B, a fluorescence signal (e.g., the relative emission intensity) of the pH adjusted sample is measured ("Signal #2") using the same excitation wavelength and with emission intensity measured at the same wavelength as the measurement taken in step 104A. In Option 1 shown FIG. 1, fluorometry analyses is conducted in parallel on aliquots of the extracted sample. In another option shown in FIG. 2 (Option 2), the steps can be performed in series, wherein a sequence of steps 104A, 103, and 104B can be performed on the extracted sample of step 102. In one option, the fluorescence signal can be measured, for example, in steps 104A and 104B using the same instrument or type of instrument, settings, conditions, and emission intensity scale so that the results can be normalized. In step 105, the fluorescence signal of the extracted signal can be corrected for background noise and interference by subtracting the signal of nonacidified sample (i.e., Signal #1) from the pH adjusted sample (i.e., Signal #2). Suspended debris and solids in the sample can cause the noise and interference encountered during the fluorescence measurements. Using the difference signal as described above, the background noise and interference may be reduced or eliminated; and by changing the pH, the fluorescence signal is maximized for optimum sensitivity. In step 106, a concentration of the tagged polymer in the extracted sample can be determined using the corrected fluorescence signal of step 105. Alternatively, the concentration of the tagged polymer can be determined, such as in a more approximated non-corrected manner, directly from step 104B without correction of step 105 (not shown). Knowing the proportion of added tagged polymer and the least one different water treatment chemical in the originally added treatment composition, a concentration of the at least one different water treatment chemical also is determinable from the determined concentration of the tagged polymer. In the method, the concentration of the tagged polymer can be proportionally correlated to a single different treating chemical or multiple different treatment chemicals. In step 107, the determined concentration of the tagged polymer (e.g., fluorescent polymer) is compared to a selected low limit set point (or selected concentration range). If the determined concentration is less than the selected low limit set point (or selected concentration range), the concentration of the tagged polymer as well as any optional other water treatment compounds in the formulation can be adjusted, in step 108, by adding to the aqueous system fresh amounts of these components in the same selected or known ratio "x" or proportion as that used in step 101. If the concentration is determined not to be below the set point, the adjustment step 108 is skipped. The succession of steps 102-108 can be repeated any number of times over a monitoring period on a regular or random basis. The method can maintain amounts of the water treatment composition in the aqueous system in amounts wherein it can interact with the aqueous system sufficiently to control the growth of at least one fouling material in the aqueous system.

For purposes of conducting the fluorometry analysis steps 104A and 104B in FIG. 1, conventional methods can be adapted for use to predetermine the wavelength of maximum absorption (usually the same as the excitation maximum) and the wavelength of maximum relative emission intensity of the tagged polymer comprising the fluorophore (i.e., the fluorescent polymer). A fluorescent monomer (or component) of the tagged polymer, which is described in more detail in other sections herein, can be the sole or primary source of the fluorescence property of the tagged polymer that is spectroscopically detected and analyzed in the present methods. A concentration of the extracted sample can be calculated, for example, by comparison of the measured relative intensity value for the extracted sample to a relative emission intensity value observed for at least one standardized formulation of known concentration of the tagged polymer with its other active co-ingredients using the same instrument and settings. The correlation of concentrations of the tagged polymer and relative emission intensity values, such as determined by fluorometry methods indicated herein, is treated as a direct or linear function. For example, if the relative emission intensity value measured for an extracted sample is 10, and a standardized sample containing the same water treatment chemicals including the tagged polymer in a known concentration (e.g., 5 ppm tagged polymer) has a relative emission intensity value under similar excitation and emission measurement conditions of 20, then it can be calculated that the extracted sample has a tagged polymer concentration of 2.5 ppm tagged polymer (e.g., $j=5\times(10/20)=2.5$ ppm), where j is the unknown concentration of the tagged polymer in the extracted sample to be calculated). Further, where the tagged polymer is optionally used in a known ratio or proportion to other water treatment chemicals, the determination of the concentration of the fluorescent component in the extracted sample in methods such as indicated, permits the concentrations of other different treatment chemicals to be calculated in a straightforward manner based on their known use ratio. For example, if the tagged polymer is used in treating an aqueous system at a known or constant addition ratio of 1:10 relative to a non-tagged treatment polymer (e.g., the non-tagged polymer is similar except does not include the fluorescent monomer), a determined concentration of 1 ppm for the tagged polymer in an extracted sample permits the concentration of the non-tagged polymer to be calculated as being 10 ppm consistent with their indicated known use ratio (i.e., 1:10).

Figure 2:
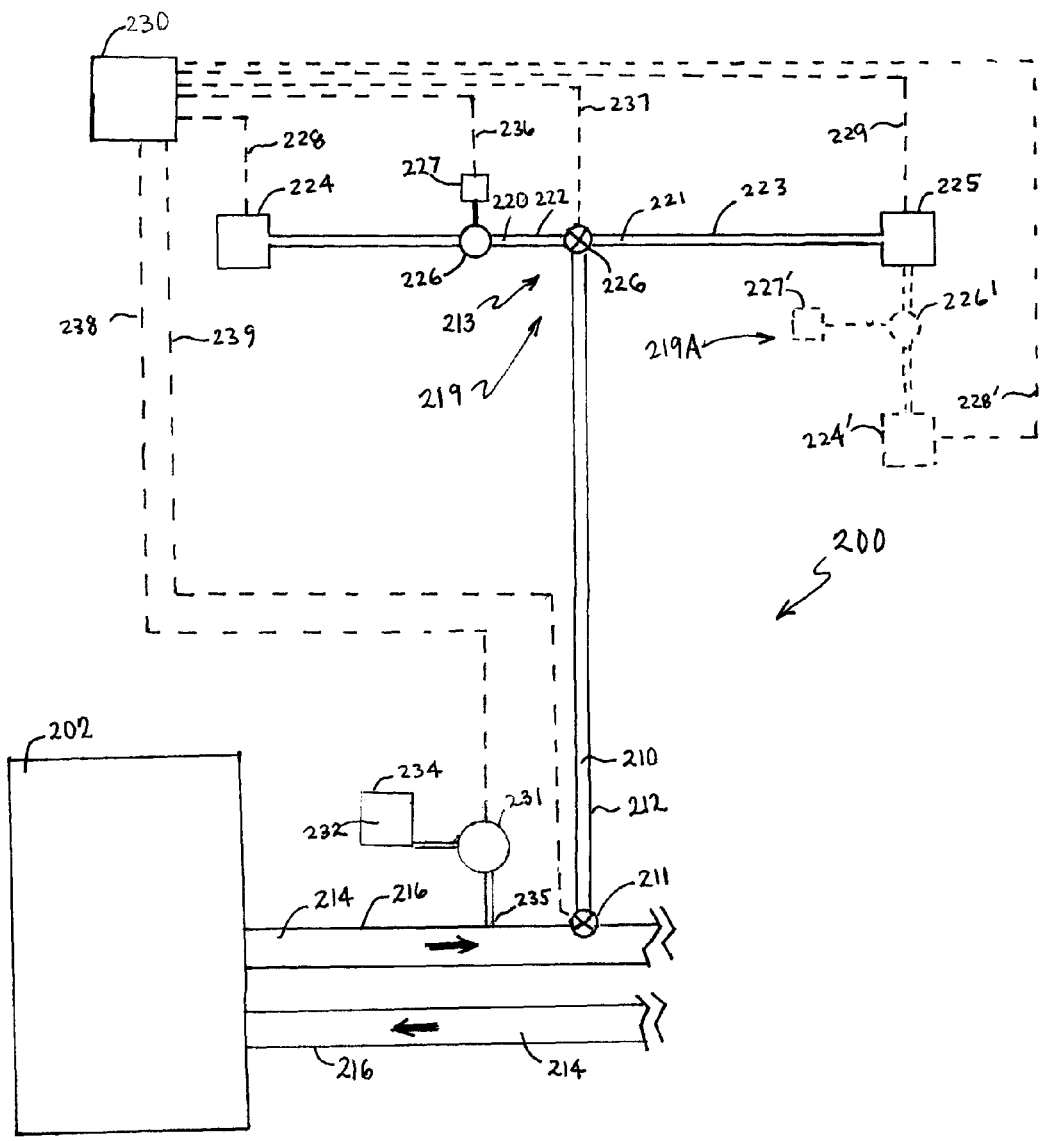
FIG. 2 is a schematic view of a system for conducting a method of FIG. 1.

A system for automatically dosing a water treatment composition including a tagged polymer into an aqueous system according to an option of the present invention is shown in FIG. 2. As depicted in FIG. 2, a water coolant system 200 can comprise a water cooling apparatus 202, for example, a water cooling tower. Coolant water 214, which contains the treatment composition and components thereof such as exemplified herein, circulates through pipes or conduits 216 forming part of the cooling system 200 (shown in part). A portion of the fluid circulating in conduits 216, for example, can be diverted as a stream 210 from conduit 216, e.g., using a control valve 211, which controls diverted fluid flow into tap conduit 212. Stream 210 can be diverted into a side-stream analysis system 219 for fluorometry scanning and concentration quantitation of the treatment agents. The diverted stream 210 can be introduced into a T-shaped piping section 213 which feeds respective portions 220 and 221 of the diverted fluid sample 210 through respective conduit branches 222 and 223. Conduits 222 and 223 feed the split fluid streams to a first fluorometer (fluorescence spectrometer) 224 and a second fluorometer 225, respectively. A control valve 226 (two-way or one-way as explained herein) can be used to control flow movement to both or either one of conduit branches 222 and 223. In one option, the valve 226 is set to permit flow of diverted stream 210 into both branches 222 and 223. The feed portion 220 in branch 222 is pH adjusted at station 226 before introduction into the first fluorometer 224. For example, acid supply (or base supply) and introduction device/system 227 can introduce sufficient acid (or base) to the sample to lower (or raise) the pH of the sample. In the case of using acid, the pH can be adjusted to from about 1 to about 3, or other acidic pH's (e.g., 0.1 to 6.9). The acid can be a mineral acid, inorganic acid, or organic acid, and can be, e.g., sulfuric acid, hydrochloric acid, nitric acid, citric acid, or other acids. The acid can be selected as an acid which does not degrade the tagged polymer before the fluorescence measurement can be completed in fluorometer 224. Similarly, if a base is used to adjust pH, the base can be selected such that the base will not degrade the tagged polymer before the fluorescence measurement is made. The base can be any type of base, such as potassium hydroxide, barium hydroxide, cesium hydroxide, sodium hydroxide, strontium hydroxide, calcium hydroxide, magnesium hydroxide, lithium hydroxide, rubidium hydroxide, and/or chemicals capable of raising the pH of the solution containing the tagged polymer. The feed portion 221 fed in branch 223 to the second fluorometer 225 is not pH adjusted, and is measured at the aqueous system pH (e.g., about 7.0 or 7 or higher). Each fluorometer can comprise a conventional design or other comparable suitable configuration adapted to measure a fluorescence property (e.g., relative emission intensity) on the present tagged polymers. For example, an apparatus which can be adapted for use for measuring active fluorescence of the samples extracted from the aqueous system can be a solid-state device such as shown in U.S. Pat. No. 7,301,158 B1, assigned to Turner Designs, Inc., Sunnyvale, Calif., which is incorporated herein by reference in its entirety. The configuration of the fluorometers can comprise, for example, a sample holder cell or cuvette located between a light emitting diode which can generate light at an excitation wavelength relevant to the tagged polymer (e.g., the excitation maximum), and, on the opposite side of the sample cell, a bandpass filter and photodiode detector for detection of emitted light at an emission wavelength relevant to the tagged polymer (e.g., the emission maximum).

Alternatively, in option 219A, the fluorometers 225 and 224' (similar to fluorometer 224) can be arranged in series as shown in dashed lines in FIG. 2. In this alternative, measurement of the non-pH adjusted sample occurs (e.g., about pH 7 or above 7 of an aqueous system) first at fluorometer 225, followed by pH adjustment (e.g., acidification) of the sample at station 226' (similar to station 226), and then re-measurement is made at adjusted pH at fluorometer 224' (similar to fluorometer 224). Samples scanned in fluorometers 224 and 225 can be flushed or otherwise removed in any convenient manner before the next sample is introduced therein for scanning.

In FIG. 2, the communication lines 228, 229, and 236-239 represent communication lines between a controller 230 and the various devices described herein, such for transmitting signals on sensed values, control commands, or both, depending on the device. The communication lines may be hardwired, radio frequency, internet, or other means. Output signals 228 and 229 from fluorometers 224 and 225, or if applicable signals 228' and 229 from fluorometers 224' and 225, are interfaced to controller 230. The controller 230 can comprise a digital programmable computer processor with memory, which can process and interpret the fluorescence signals acquired from the fluorometers. The controller 230 can be configured, for example, to apply algorithms to the output signals received from the fluorometers for calculating the difference of the signals to correct for background noise. The controller 230 can be programmable to correlate the corrected output signal with a concentration of the tagged polymer (e.g., fluorescent polymer) in the extracted sample. The concentration of at least one different water treatment compound added in a known proportion with the tagged polymer into the aqueous system can be calculated from the concentration of the tagged polymer that has been determined. Based on these determinations of the concentration of at least the tagged polymer and the at least one different water treatment chemical (e.g., polymer), one or both of the determined concentrations can be compared to a low limit set point or selected concentration range inputted and stored in the controller. These inputs may be entered, for example, by a keypad onboard the controller (not shown), remotely through a graphical user interface or keypad of another device in communication with the controller (not shown), or may be included in programming loaded into the controller. If the comparisons show that the concentration(s) have fallen below the low limit set point or selected range, a signal can be outputted from the controller 230 to actuate the operation of a chemical pump 231 to add fresh additional water treatment product 232 stored in a supply container 234 into the aqueous system. The fresh additional water treatment product 232 contains the tagged polymer or the tagged polymer and the at least one different water treatment chemical (e.g., polymer) in a preselected proportion. Although FIG. 2 illustrates a single point of introduction 235 for the addition of fresh water treatment product into the water coolant system 200, multiple points can be provided, for example, at different convenient locations within the water coolant system 200. Also, although the illustration in FIG. 2 shows common introduction of the tagged polymer or the tagged polymer and at least one different water treatment compound in the form of a pre-mixed product 232, the different ingredients and compounds can be separately introduced in a coordinated manner using controller 230 using separate dedicated supplies and pumps (not shown). As indicated, the concentration of the tagged polymer can be proportionally correlated to a single different treating chemical or multiple different treatment chemicals. The amount of make-up fresh composition added to the aqueous system may be a fixed amount, or an amount calculated by the controller using a programmed algorithm to compensate for the shortfall measured for the extracted sample versus the low limit set point or target value.

As indicated, the present invention is based in part upon the discovery of tagged treatment polymers containing certain fluorescent monomers which are useful in their preparation, with the tagged treatment polymers being able to provide the ability to monitor in industrial water systems and other aqueous systems at relatively low concentrations (e.g., at less than 100 ppm tagged polymer, at less than 50 ppm tagged polymer, or less than 25 ppm tagged polymer, or less than 10 ppm tagged polymer, or less than 7 ppm tagged polymer, or less than 5 ppm tagged polymer, or less than 4 ppm tagged polymer, or less than 3 ppm tagged polymer, or from 1 ppm to 25 ppm tagged polymer, or other values). "Tagging" the polymer through the use of the fluorescent monomers of this invention can be achieved, for example, by synthesizing the polymer in the presence of at least one fluorescent monomer wherein the fluorescent monomer forms a monomeric unit of the synthesized polymer structure. The fluorescent monomer, as one option, can be a natural compound which can be directly incorporated into the polymer without derivatization. The fluorescent monomer can provide a chemically reactive moiety, such as, for example, a terminal olefinic group, which can be used for the incorporation of the monomer into the tagged polymer. The chemically reactive moiety can be a terminal ethylenic unsaturation containing group, and can be optionally attached to a ring structure. The fluorescent monomer should be responsive to at least one wavelength of light that can be monitored with a fluorometer and can be pH sensitive as described herein. Although the following illustration shows two different types of non-fluorescent monomers, it will be appreciated that there is no limit on the number of different types of non-fluorescent monomers which can be incorporated into the tagged polymer with the fluorescent monomer. For example, the number of different types of non-fluorescent monomers incorporated into the tagged polymer with the fluorescent monomer may be one, two, three, four, five, or higher numbers. It also is possible to incorporate more than one type of fluorescent monomer into the tagged polymer, wherein the different types of fluorescent monomers can be selected, for example, to respond to different wavelengths of light which can be monitored by a fluorometer. The fluorescent polymer or tagged polymer can be, for example, a water-soluble polymer.

As an option, the tagged polymer contains units derived, for example, from a fluorescent monomer as indicated herein; with or without any of the following: (1) a carboxylic monomer or salts thereof; (2) a unit derived from certain carboxyl-free monomers or salts thereof, (3) unsaturated non-ionizable type monomers, or (4) their combinations.

The tagged treatment polymer can be, for example, of the formula:

$$X_a Y_b Z_c \qquad (I)$$

wherein c has a positive, nonzero value (i.e., values>0). As an option, formula (I) represents a terpolymer, wherein a, b, and c are all positive values. Each of X, Y, and Z may be solely one type of monomer, or one or more of X, Y, and Z can be represented in the polymer by different types of monomers within each category.

Each X or Y in formula (I) independently can be acrylic acid, methacrylic acid, maleic acid, maleic anhydride, crotonic acid, itaconic acid, vinylacetic acid, fumaric acid, tetrahydrophthalic anhydride, or salts thereof, acrylamide, methacrylamide, 2-acrylamido-2-methyl-1-propanesulfonic acid ("AMPS"), 2-methacrylamido-2-methyl-1-propanesulfonic acid, 3-methacrylamido-2-methyl-1-propanesulfonic acid, tertbutylacrylamide, isopropylacrylamide, tetraoctylacrylamide, butoxymethylacrylamide, dimethylacrylamide, diethylacrylamide, N-alkyl-(meth) acrylamide, N-alkanol(methyacrylamide, N,N-dialkyl(meth) acrylamide, dimethylaminopropyl acrylamide methyl sulfate quaternary salts, dimethylaminopropyl methacrylamide methyl sulfate quaternary salts, diallyldimethyl ammonium chloride (DADMAC), dimethyldiallyl ammonium chloride (DMDAAC), vinyl formamide, methacrylamidopropyl trimethyl ammonium chloride, acrylamidopropyl trimethyl ammonium chloride, methylene bis acrylamide, triallylamine, acid salts of triallylamine, ethyl acrylate, butyl acrylate, t-butyl(meth)acrylate, N-alkyl(meth)acrylate, 2-hydroxy N-alkyl(meth)acrylate, N-alkanol-N-alkyl(meth) acrylate, ethylene glycol dimethacrylate, hydroxymethylacrylate, hydroxyethylacrylate, hydroxypropylacrylate, hydroxypropylmethacrylate, diethylene glycol dimethacrylate, triethylene glycol dimethylacrylate, alkoxyethyl acrylate, polyethylene glycol monomethacrylate, polyethylene glycol dimethacrylate, glycidyl methacrylate, alkyl vinyl ether, acrylamidomethylpropane sulfonic acid and the sodium salt thereof, dimethylaminoethyl acrylate methyl chloride quaternary salts, dimethylaminoethyl acrylate benzyl chloride quaternary salts, dimethylaminoethyl acrylate methyl sulfate quaternary salt, dimethylaminoethyl methacrylate methyl sulfate quaternary salt, dimethylaminoethyl acrylamide methyl sulfate quaternary salts, styrene sulfonic acid, vinyl sulfonic acid, allyl sulfonic acid, 3-allyloxy-2-hydroxypropane sulfonic acid, vinyl alcohol, vinyl acetate, N-vinylpyrrolidone, vinyl-2-pyrrolidone, or salts thereof, or derivatives thereof, or any combinations thereof. X or Y can be, for example, an unsaturated carboxylic monomer, e.g., a monoethylenically unsaturated monocarboxylic monomer or a monoethylenically unsaturated dicarboxylic monomer; or a monomer providing unsaturated non-ionizable monomer units in the compounds of formula (I), such as (meth)acrylamide and the like. X or Y can be, for example, a carboxyl-free monomer, such as AMPS and the like. The salts can be, for example, sodium, potassium, or ammonium salts.

Each Z in formula (I) independently can be a fluorescent unit derived from a fluorophore monomer having at least one terminal end comprising an olefinic group or salt thereof (e.g., an ethylenic unsaturation containing group, optionally attached to a ring structure. The salt can be, for example, sulfate, hydrochloride, dihydrochloride, bisulfate, or gluconate. As an option, the olefinic group is a reactive terminal group of the structure.

Examples of the fluorophores include, for example, quinine and isomers thereof, such as quinidine. As an option, Z can be derived from compounds such as quinine, having at least one hydroxyl group (e.g., one hydroxyl group (—OH), or two hydroxyl groups, or more), wherein this hydroxyl functionality is maintained in the residue of the quinine or other monomer that forms moiety Z of the tagged treatment polymer (I).

Figure 3:
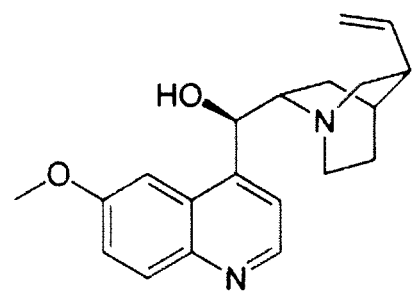
FIG. 3 shows chemical structures of quinine and quinidine.
Figure 3:
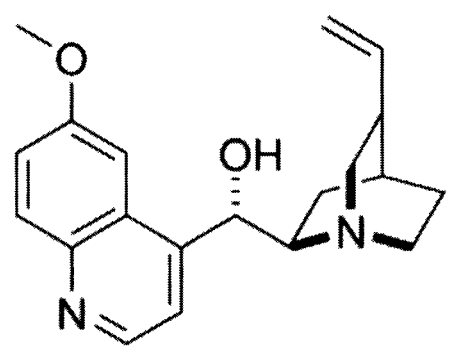

FIG. 3 shows exemplary structures of quinine and quinidine. These types of compounds have the indicated desired structure including having at least one terminal end with an olefinic group (e.g., ethylenic unsaturation), which can be incorporated into the tagged polymers without needing further derivatization in advance of their use in the synthesis of the tagged polymer. As indicated, quinine is a natural compound and it also can be synthesized. As shown in FIG. 3, quinine contains two major fused-ring systems, which are aromatic quinoline and the bicyclic quinuclidine. An IUPAC name for quinine is (R)-(6-methoxyquinolin-4-yl)((2S,4S,8R)-8-vinylquinuclidin-2-yl)methanol. Quinine has been described under CAS No. 130-95-0. Quinine is a basic amine and usually is presented as a salt. Various salt forms that exist include, for example, quinine sulfate, quinine hydrochloride, quinine dihydrochloride, quinine bisulfate, and quinine gluconate. Quinine dosing can take into account the particular salt form of a quinine source in calculating the quinine content obtained therefrom. Quinidine, a stereoisomer of quinine, can have the IUPAC name (9S)-6'-methoxycinchonan-9-ol. It has been described under CAS No. 56-54-2. Other fluorophores may be used which have at least one terminal end comprising an olefinic group, such as a ring structure which can comprise a multiple fused ring system.

As an option, formula (I) can contain monomeric units of groups Y and Z, X and Z, X, Y and Z, or Z alone. As an option, the monomeric unit X, or monomeric unit Y, or the combination of monomeric units X and Y, in the tagged polymer of formula (I), can have a fouling control property or effect in an aqueous system being treated.

In formula (I), as an option, "a" and "b" can be from 0 to about 99, and "c" can be from about 0.001 to about 100. The sum of a, b, and c can be 100, or other lesser values if additional monomers are incorporated into the polymer.

As an option, the tagged polymer or fluorescent polymer can be a terpolymer of quinine or an isomer thereof, acrylic acid, and acrylamide. The tagged polymer or fluorescent polymer can comprise, for example, from about 0.5 to about 10 parts by weight quinine or an isomer thereof, from about 80 to about 99 parts by weight acrylic acid, and from about 1 to about 10 parts by weight acrylamide, based on total parts by weight of said polymer, or from about 1 to about 8 parts by weight quinine or an isomer thereof, from about 84 to about 94 parts by weight acrylic acid, and from about 2 to about 8 parts by weight acrylamide, based on total parts by weight of said polymer, or from about 3 to about 7 parts by weight quinine or an isomer thereof, from about 87 to about 93 parts by weight acrylic acid, and from about 3 to about 7 parts by weight acrylamide, based on total parts by weight of said polymer.

These tagged treatment polymers can be synthesized, for example, by adapting procedures for conventional free radical polymerization in an aqueous medium, such as described herein. The polymers can be first created with the X and Y moieties of Formula (I), and the fluorescent monomer can be added in a later stage of the polymer synthesis reaction. For example, for those tagged treatment polymers containing acrylic acid and acrylamide, the polymers can be first synthesized with acrylamide and acrylic acid monomers, and then the fluorescent monomer can be added during a later stage of the same synthesis. In alternate options, the fluorescent monomer can be added at other stages of the polymer synthesis reaction, such as in the initial stage and/or at one or more subsequent stages throughout the synthesis.

General procedure for the continuous-feed manufacture of tagged treatment polymers can be as follows. U.S. Pat. No. 6,312,644 B1 and U.S. Pat. No. 6,310,156 B1, incorporated in their entirety by reference herein, can be adapted to the present invention's chemistry and uses. A water soluble polymer is obtained by conducting a polymerization reaction using hydrophilic monomers containing acrylic acid, acrylamide, or other water soluble monomers along with a combination of a persulfate salt and a bisulfite as initiators at reduced pH. The types and quantities of specific components in the formula (monomers, for example) will vary depending upon the type of polymer (cationic, anionic, nonionic) that is being synthesized.

As an example, the desired initial water can be charged to the reaction vessel, which can be equipped with a mixer, a thermocouple, a nitrogen purging tube, and a water condenser. A nitrogen purge may be applied with vigorous stirring. Heating begins until the desired temperature is reached, as specified by the molecular weight and viscosity desired. While temperature and stirring are maintained, separate feeds of the redox initiators (e.g., a persulfate salt and a bisulfite salt) at constant rate are begun. After ten minutes or other suitable time, monomers can be added continuously at constant rate along with initiators. After the desired amount of monomers is added by weight or by volume over a three hour period or other period, the monomer addition can be stopped while the initiator feed continues another ten minutes to promote completion of the reaction. In making a quinine-labeled polymer, an ethanol solution of quinine can be added, for instance, during the final thirty minutes of monomer co-feed. The reaction temperature can be maintained for an additional hour after the stopping of initiator co-feed. The pH is adjusted to the desired level by the addition of strong base. The batch weight is measured, and water added to maintain a polymer concentration of, for example, 45-50%. The material can be sampled to verify viscosity, pH, percent solids, reduced viscosity, and residual monomer concentration.

As an option, the tagged polymers can be synthesized in a batch process as well. General procedure for the batch-mode manufacture of water-soluble tagged treatment polymers can be as follows. The types and quantities of specific components in the formula (monomers, for example) can vary depending upon the type of polymer (cationic, anionic, nonionic) that is being synthesized. An aqueous solution containing one or more water-soluble monomers, as well as any polymerization additives, such as chelants, pH buffers, and/or chain transfer agents, can be charged to a reaction vessel equipped with a mixer, a thermocouple, a nitrogen purging tube, and a water condenser. The monomer solution can be mixed vigorously, heated to the desired temperature, and then a water-soluble initiator can be added. The solution can be purged with nitrogen while maintaining temperature and mixing for several hours. In order to synthesize the present tagged treatment polymers, the fluorescent monomer is added, such after addition of the other monomers, such as during the about the last 30 minutes of the reaction. After this time, the products are cooled to room temperature, and any post-polymerization additives are charged to the reactor.

All molecular weights herein are weight average molecular weights measured by gel permeation chromatography (GPC) unless indicated otherwise. Tagged treatment polymers that have a wide range of molecular weights can be prepared, such as by the methods described and referenced herein. The molecular weights (average molecular weight—in Daltons) of the present tagged treatment polymers can be, for example, from about 500 to about 20,000 or more, or from about 2000 to about 20,000, or from about 5000 to about 20,000, or from about 10,000 to about 20,000, or other molecular weights.

The tagged polymer comprising a fluorescent monomer may be used in the industrial water systems singly or in combination with other polymers, which are not tagged. The wording "not tagged" means the compound does not include the fluorescent monomer being monitored. The dosage rate of tagged treatment polymer in an industrial water system, such as a cooling water system, such as when it is being used to control scale or other fouling material, can be, for example, from about 0.1 to about 100 ppm, or from about 0.5 to about 50 ppm, or from about 0.75 to about 25 ppm, or from about 0.9 to about 15 ppm, or from about 1 to about 5 ppm, of active solid component. The proportion (as a weight ratio) of tagged polymer to other non-tagged water treatment agents optionally used in combination with the tagged polymers in a selected or known proportion can range, for example, from about 1:1 to about 1:100 tagged polymer/different treatment agent, or from about 1:2 to about 1:25 tagged polymer/different treatment agent, or from about 1:3 to about 1:15 tagged polymer/different treatment agent, or from about 1:4 to about 1:10 tagged polymer/different treatment agent, or other weight ratios thereof. These usage amounts and ratios may vary, for example, depending on the chemistry of the water treatment compounds, the fouling material to be controlled, and the type of aqueous system, wherein suitable usage values can be determined by a skilled person in view of the disclosures herein.

The water treatment chemical (or chemicals) which can be used in combination with the tagged polymer is not necessarily limited. They may be organic or inorganic. The water treatment chemical can be a polymer. The water treatment chemical can be a polymer similar in the chemistry of the monomeric units thereof relative to the tagged polymer except the polymer omits the fluorescent monomer content.

Examples of fouling materials which can be controlled using the present methods and fluorescent tagged polymers include, for example:

scaling and/or precipitation fouling, as crystallization of solid salts, oxides, and hydroxides from water solutions, for example, calcium carbonate or calcium sulfate;

particulate fouling, i.e., accumulation of particles, typically colloidal particles, on a surface;

corrosion fouling, e.g., in-situ growth of corrosion deposits, for example, magnetite on carbon steel surfaces;

chemical reaction fouling, for example, decomposition or polymerization of organic matter on heating surfaces;

solidification fouling, such as when components of the flowing fluid with a high-melting point freeze onto a sub-cooled surface;

biofouling, such as settlements of bacteria and algae; and composite fouling, which involves more than one foulant or fouling mechanism.

Some types of scale and precipitation fouling deposits which can be controlled in aqueous systems using methods and tagged polymers of the present invention include, for example, calcium sulfate (e.g., anhydrite, hemihydrate, gypsum), barium sulfate, calcium carbonate (e.g., calcite, aragonite), calcium oxalate, magnesium hydroxide, magnesium oxide, silicates (e.g., serpentine, acmite, gyrolite, gehlenite, amorphous silica, quartz, cristobalite, pectolite, xonotlite), aluminum oxide hydroxides (e.g., boehmite, gibbsite, diaspore, corundum), aluminosilicates (e.g., analcite, cancrinite, noselite), copper (e.g., metallic copper, cuprite, tenorite), phosphates (e.g., hydroxyapite), magnetite, or nickel ferrite.

The method of the present invention may be used in industrial or recreational aqueous systems requiring scale control or other fouling control. Such aqueous systems include, but are not limited to, cooling water systems (cooling towers, intake cooling waters, and effluent cooling waters), heat exchangers, boilers, water heaters, recirculating water systems, fire control water systems, retorts, air washers, water storage systems, swimming pools, hot tubs, decorative fountains, cooling lagoons and other aqueous systems. In general, any industrial, recreational or residential water system can benefit from the present invention.

Although embodiments are shown wherein the fluorescent monomer compound, such as quinine or an isomer thereof, is incorporated chemically into a treatment polymer which includes different monomer materials, it is also is possible to use the fluorescent compound in free form (e.g., as a marker/tracer only and not as an active ingredient) in the aqueous system which is being treated and monitored for treatment compound concentrations.

The present invention includes the following aspects/embodiments/features in any order and/or in any combination:

1. The present invention relates to a method of controlling the concentration of water treatment composition in an aqueous system, comprising:

(a) introducing into said aqueous system, a water treatment composition comprising at least one tagged polymer to provide treated water, wherein the tagged polymer comprises at least one fluorescent monomeric unit derived from a fluorophore having at least one terminal end comprising an olefinic group;

(b) extracting a sample of the treated water;

(c) measuring a background fluorescence signal of the extracted water;

(d) adjusting the pH of the extracted sample to provide a pH adjusted sample having an enhanced fluorescence signal;

(e) measuring the enhanced fluorescence signal;

(f) determining a concentration of the tagged polymer in the sample using the difference between the fluorescence signals measured in (c) and (e) above;

(g) introducing a fresh amount of the water treatment composition into the aqueous system, if the concentration of the tagged polymer determined in (f) is below a selected set point, wherein the water treatment composition controls growth of at least one fouling material in the aqueous system.

2. The method of any preceding or following embodiment/feature/aspect, wherein the water treatment composition further comprises at least one different water treatment chemical.

3. The method of any preceding or following embodiment/feature/aspect, wherein the fluorophore comprises quinine or an isomer thereof.

4. The method of any preceding or following embodiment/feature/aspect, wherein the fluorophore comprises quinine or quinidine.

5. The method of any preceding or following embodiment/feature/aspect, wherein the tagged polymer is a copolymer or terpolymer of (a) quinine or an isomer thereof, and (b) at least one monomer that is acrylic acid or salt thereof, methacrylic acid or salt thereof, maleic acid or salt thereof, maleic anhydride, crotonic acid or salt thereof, itaconic acid or salt thereof, acrylamide, methacrylamide, 2-acrylamido-2-methylpropane sulfonic acid (AMPS) or salt thereof, polyethylene glycol monomethacrylate, vinyl phosphonic acid or salt thereof, styrene sulfonic acid or salt thereof, vinyl sulfonic acid or salt thereof, 3-allyloxy-2-hydroxypropane sulfonic acid or salt thereof, N-alkyl-(meth)acrylamide, t-butyl(meth)acrylate, N-alkyl(meth)acrylate, N-alkanol-N-alkyl(meth)acrylate, dimethyldiallyl ammonium chloride (DMDAAC), diallyldimethyl ammonium chloride (DADMAC), vinyl acetate, 2-hydroxy N-alkyl(meth)acrylate, alkyl vinyl ether, alkoxyethyl acrylate, N-alkanol(methyacrylamide, N,N-dialkyl(meth)acrylamide, vinyl-2-pyrrolidinone, or any combinations thereof.

6. The method of any preceding or following embodiment/feature/aspect, wherein the tagged polymer comprises from about 0.5 to about 10 parts by weight quinine or an isomer thereof, from about 80 to about 99 parts by weight unsaturated carboxylic monomer, and from about 1 to about 10 parts by weight acrylamide, based on total parts by weight of said tagged polymer.

7. The method of any preceding or following embodiment/feature/aspect, wherein the water treatment composition comprises from about 0.1 wt % to about 100 wt % of the tagged polymer and from about 0 wt % to about 99.9 wt % of at least one different water treatment chemical.

8. The method of any preceding or following embodiment/feature/aspect, wherein the tagged polymer is maintained in the aqueous system within a concentration range of from about 1 ppm to about 200 ppm.

9. The method of any preceding or following embodiment/feature/aspect, wherein the at least one different water treatment chemical is maintained in the aqueous system within a concentration range of from about 5 ppm to about 100 ppm.

10. The method of any preceding or following embodiment/feature/aspect, further comprising step (g): repeating steps (b)-(g) at least once.

11. The method of any preceding or following embodiment/feature/aspect, wherein the measuring of the fluorescence signal comprises exciting the pH adjusted sample with light at an excitation wavelength and detecting emitted light intensity at an emission wavelength of light emitted by the pH adjusted sample.

12. The method of any preceding or following embodiment/feature/aspect, further comprising correcting the measured emitted light intensity of the pH adjusted sample by subtracting a separately measured emitted light intensity of an extracted sample of the treated water which has not been pH adjusted.

13. The method of any preceding or following embodiment/feature/aspect, wherein the excitation wavelength is about 345 nm and the emission intensity wavelength is about 450 nm.

14. The method of any preceding or following embodiment/feature/aspect, wherein the at least one different water treatment chemical controls a fouling material in the aqueous system that comprises scale.

15. The method of any preceding or following embodiment/feature/aspect, wherein the at least one different water treatment chemical controls scale in the aqueous system.

16. The method of any preceding or following embodiment/feature/aspect, further comprising:
(i) providing at least one sampling location where fluid extracted from the aqueous system is subjected to spectrofluorometric analysis with a fluorometer to measure the fluorescence signal; and
(ii) providing a controller operable to automatically control introduction of additional water treatment composition into the aqueous system from a material supply based on the measured value of the fluorescence signal of the extracted sample.

17. The present invention relates to a method of controlling the growth of at least one fouling material in an aqueous system, comprising:
providing a water treatment composition in an aqueous system, wherein the composition comprises a nonpolymerized quinine and at least one water treatment chemical in a selected proportion;
determining a concentration of said at least one water treatment compound in said aqueous system using a measured fluorescence signal of the nonpolymerized quinine; and
maintaining a concentration of said water treatment compound in said aqueous system within a selected concentration range based on a result of said measured fluorescence signal of the nonpolymerized quinine,
wherein the water treatment composition interacts with the aqueous system to control the growth of at least one fouling material in the aqueous system.

18. The present invention relates to a tagged polymer for treatment of water, comprising at least one pH-sensitive fluorescent monomeric unit derived from a pH-sensitive fluorophore having at least one terminal end comprising an olefinic group.

19. The tagged polymer of any preceding or following embodiment/feature/aspect, wherein the fluorophore comprises quinine or an isomer thereof.

20. The tagged polymer of any preceding or following embodiment/feature/aspect, wherein the fluorophore comprises quinine or quinidine.

21. The tagged polymer of any preceding or following embodiment/feature/aspect, wherein said tagged polymer is a copolymer or terpolymer of quinine or an isomer thereof, and one or more other monomer.

22. The tagged polymer of any preceding or following embodiment/feature/aspect, wherein the tagged polymer comprises from about 0.5 to about 10 parts by weight quinine or an isomer thereof, from about 80 to about 99 parts by weight unsaturated carboxylic monomer, and from about 1 to about 10 parts by weight acrylamide, based on total parts by weight of said polymer.

23. The present invention relates to a water treatment composition comprising a tagged polymer, wherein the tagged polymer comprises at least one pH-sensitive fluorescent monomeric unit derived from a pH-sensitive fluorophore having at least one terminal end comprising an olefinic group, and said tagged polymer is capable of water treatment in an aqueous system.

24. The water treatment composition of any preceding or following embodiment/feature/aspect, wherein the fluorophore comprises quinine or an isomer thereof.

The present invention can include any combination of these various features or embodiments above and/or below as set forth in sentences and/or paragraphs. Any combination of disclosed features herein is considered part of the present invention and no limitation is intended with respect to combinable features.

The present invention will be further clarified by the following examples, which are intended to be exemplary of the present invention.

EXAMPLES

Example 1

Experiments were conducted to fluorometrically analyze tagged polymers in aqueous systems. The tagged polymers were monitored in the systems when used at different concentrations and over a period of time in the systems. These experiments involved four runs, referred to herein as Runs A, B, C, and D. The different tested aqueous systems were dilute acid (0.05 N $H_2SO_4$, pH 1.86), cooling tower water (acidified to pH 1.86), and chlorinated waters at 150 ppm $Cl^-$ and 500 ppm $Cl^-$. Fluorometry results of the studies are summarized in Table 1 shown in FIG. 4.

For these experiments, a quinine-monomer tagged acrylic acid/acrylamide terpolymer was prepared using the same synthesis method. The tagged treatment polymer was synthesized by adapting procedures for conventional water soluble polymer synthesis, such as described herein. In each case, acrylic acid, acrylamide, and the redox catalyst were added simultaneously and continuously over a period of three hours. During the last thirty minutes of this time period, a solution of quinine hydrochloride in ethanol was also added simultaneously and continuously as well. The total added proportions of the three monomers were 5 parts by weight quinine, 91 parts by weight acrylic acid, and 5 parts by weight acrylamide, based on total parts by weight of the polymer.

The tagged polymer was tested at different concentrations (1 ppm, 5 ppm, 10 ppm, 20 ppm) in several different aqueous systems at 24 hours (day 1), 48 hours (day 2), and 120 hours (day 5) as indicated in Table 1 shown in FIG. 4. Water samples extracted from the cooling tower were acidified to pH 1.86 with 0.05 N sulfuric acid, and then analyzed for emission intensity with a fluorometer. Duplicates of the extracted samples are measured without acidification to obtain a measure of the background noise and interference. These results were subtracted from the emission values measures for the acidified samples, and the difference is reported as the result shown in Table 1.

Extracted samples were analyzed using a Perkin-Elmer Model LS-5B spectrofluorometer, with the excitation wavelength set at 345 nm; and the emitted light was measured at 450 nm, and relative emission intensity was measured with the same device. The emission intensity values in Table 1 are based on a normalized scale. The results of these experiments are indicated in Table 1 shown in FIG. 4.

The "off scale" entries in Table 1 refer to the fluorometer readings that exceeded the upper limit of the "gain" setting selected on the instrument for displaying the read-out of the emission intensities of the samples. As generally understood, increasing the "gain" setting on a fluorometer can increase the sensitivity of the instrument, so dilutions of samples or reduction in the "gain" setting may be used to prevent off scale readings on the instrument.

The results demonstrate that the tagged polymers can be fluorometrically monitored in an accurate, reliable manner when used at relatively low concentrations in various aqueous systems.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of controlling the concentration of water treatment composition in an aqueous system, comprising:
   (a) introducing into said aqueous system, a water treatment composition comprising at least one tagged polymer to provide treated water, wherein the tagged polymer comprises at least one fluorescent monomeric unit derived from a fluorophore having at least one terminal end comprising an olefinic group;
   (b) extracting a sample of the treated water;
   (c) measuring a background fluorescence signal of the extracted water;
   (d) adjusting the pH of the extracted sample to provide a pH adjusted sample having an enhanced fluorescence signal;
   (e) measuring the enhanced fluorescence signal;
   (f) determining a concentration of the tagged polymer in the sample using the difference between the fluorescence signals measured in (c) and (e) above;
   (g) introducing a fresh amount of the water treatment composition into the aqueous system, if the concentration of the tagged polymer determined in (f) is below a selected set point,
   wherein the water treatment composition controls growth of at least one fouling material in the aqueous system.

2. The method of claim 1, wherein the water treatment composition further comprises at least one different water treatment chemical.

3. The method of claim 1, wherein the fluorophore comprises quinine or an isomer thereof.

4. The method of claim 1, wherein the fluorophore comprises quinine or quinidine.

5. The method of claim 1, wherein the tagged polymer is a copolymer or terpolymer of (a) quinine or an isomer thereof, and (b) at least one monomer that is acrylic acid or salt thereof, methacrylic acid or salt thereof, maleic acid or salt thereof, maleic anhydride, crotonic acid or salt thereof, itaconic acid or salt thereof, acrylamide, methacrylamide, 2-acrylamido-2-methylpropane sulfonic acid (AMPS) or salt thereof, polyethylene glycol monomethacrylate, vinyl phosphonic acid or salt thereof, styrene sulfonic acid or salt thereof, vinyl sulfonic acid or salt thereof, 3-allyloxy-2-hydroxypropane sulfonic acid or salt thereof, N-alkyl-(meth) acrylamide, t-butyl (meth)acrylate, N-alkyl (meth)acrylate, N-alkanol-N-alkyl (meth)acrylate, dimethyldiallyl ammonium chloride (DMDAAC), diallyldimethyl ammonium chloride (DADMAC), vinyl acetate, 2-hydroxy N-alkyl (meth)acrylate, alkyl vinyl ether, alkoxyethyl acrylate, N-alkanol (methyacrylamide, N,N-dialkyl(meth) acrylamide, vinyl-2-pyrrolidinone, or any combinations thereof.

6. The method of claim 1, wherein the tagged polymer comprises from about 0.5 to about 10 parts by weight quinine or an isomer thereof, from about 80 to about 99 parts by weight unsaturated carboxylic monomer, and from about 1 to about 10 parts by weight acrylamide, based on total parts by weight of said tagged polymer.

7. The method of claim 1, wherein the water treatment composition comprises from about 0.1 wt % to about 100 wt % of the tagged polymer and from about 0 wt % to about 99.9 wt % of at least one different water treatment chemical.

8. The method of claim 1, wherein the tagged polymer is maintained in the aqueous system within a concentration range of from about 1 ppm to about 200 ppm.

9. The method of claim 2, wherein the at least one different water treatment chemical is maintained in the aqueous system within a concentration range of from about 5 ppm to about 100 ppm.

10. The method of claim 1, further comprising step (h): repeating steps (b)-(g) at least once.

11. The method of claim 1, wherein the measuring of the fluorescence signal comprises exciting the pH adjusted sample with light at an excitation wavelength and detecting emitted light intensity at an emission wavelength of light emitted by the pH adjusted sample.

12. The method of claim 11, further comprising correcting the measured emitted light intensity of the pH adjusted sample by subtracting a separately measured emitted light intensity of an extracted sample of the treated water which has not been pH adjusted.

13. The method of claim 11, wherein the excitation wavelength is about 345 nm and the emission intensity wavelength is about 450 nm.

14. The method of claim 2, wherein the at least one different water treatment chemical controls a fouling material in the aqueous system that comprises scale.

15. The method of claim 2, wherein the at least one different water treatment chemical controls scale in the aqueous system.

16. The method of claim 1, further comprising:
(i) providing at least one sampling location where fluid extracted from the aqueous system is subjected to spectrofluorometric analysis with a fluorometer to measure the fluorescence signal; and
(ii) providing a controller operable to automatically control introduction of additional water treatment composition into the aqueous system from a material supply based on the measured value of the fluorescence signal of the extracted sample.

* * * * *